United States Patent [19]

Tan et al.

[11] Patent Number: 4,825,872

[45] Date of Patent: May 2, 1989

[54] FINGER SENSOR FOR PULSE OXIMETRY SYSTEM

[75] Inventors: Josef K. S. Tan, Tampa; Jeffrey A. Baker, Lutz; Pawel J. Beczkiewicz, Tampa; John J. George, Clearwater, all of Fla.

[73] Assignee: Critikon, Inc., Tampa, Fla.

[21] Appl. No.: 229,518

[22] Filed: Aug. 5, 1988

[51] Int. Cl.⁴ .............................. A61B 5/00
[52] U.S. Cl. ................... 128/633; 356/41; 128/665
[58] Field of Search ............... 128/666, 633, 644, 665, 128/664, 667, 689, 691, 670; 356/39, 40, 41, 42

[56] References Cited

U.S. PATENT DOCUMENTS

| | | | |
|---|---|---|---|
| 4,109,643 | 8/1978 | Bond et al. | 128/2 L |
| 4,450,843 | 5/1984 | Barney et al. | 128/670 |
| 4,653,498 | 3/1987 | New, Jr. et al. | 128/633 |
| 4,685,464 | 8/1987 | Goldberger et al. | 128/633 |

FOREIGN PATENT DOCUMENTS 2052050  1/1981  United Kingdom ............... 128/689

OTHER PUBLICATIONS

"Hewlett-Packard Introduces the New Wave in Pulse Oximetry", brochure pub. 12/87.

Primary Examiner—Max Hindenburg
Assistant Examiner—Scott Getzow
Attorney, Agent, or Firm—W. Brinton Yorks, Jr.

[57] ABSTRACT

A finger sensor for a pulse oximetry system is provided having a body of flexible, resilient polymeric material formed as a pocket. On the inside walls of the pocket toward the closed end are a LED light source and an opposing photodetector. The space within the pocket transverse to the longitudinal dimension of the pocket exhibits a relatively smaller width and a relatively greater width. As a finger is inserted into the pocket with the fingertip between the LED and the photodetector, the relatively smaller width of the pocket expands and the relatively greater width of the pocket decreases. This expansion and decrease of the pocket dimensions are resisted by the resilient polymeric material, causing the walls of the pocket containing the LED and the photodetector to securely contact and retain the finger within the pocket. The pocket preferably comprises a pocket having major walls containing the light source and photodetector adjoined on the longitudinal sides of the sensor by expansive side panels which expand and contract to engage fingers of varying sizes.

24 Claims, 3 Drawing Sheets

FINGER SENSOR FOR PULSE OXIMETRY SYSTEM

This invention relates to medical sensors for detecting physiological functions and, in particular, to an optical sensor for detecting vascular flow in a pulse oximetry system.

Pulse oximetry is a non-invasive medical technique useful for measuring certain vascular conditions. In practice of the technique, light is passed through a portion of a patient's body which contains arterial blood flow. An optical sensor is used to detect the light which has passed through the body, and variations in the detected light at various wavelengths are then used to determine arterial oxygen saturation and/or pulse rates. Oxygen saturation may be calculated using some form of the classical absorption equation known as Beer's Law.

Accurate measurements of these physiological functions are predicated upon optical sensing in the presence of arterial blood flow. Conveniently an earlobe or a finger may serve this purpose, each of which allows easy access to a body part through which light will readily pass. Local vascular flow in a finger is dependent upon several factors which affect the supply of blood. Blood flow may be affected by centrally mediated vasoconstriction, which must be alleviated by managing the perceived central causes. Peripheral constriction, however, can be induced by local causes. One such cause of local vasoconstriction is the pressure exerted by the sensor on the finger. Many currently available pulse oximetry finger sensors have a hard shell which has a high profile and is maintained on the finger by the action of a spring. Since excess pressure on the finger can dampen or eliminate the pulsations in the blood supply to the finger, these springs are intentionally made very soft. The result of this compromise is that the spring-held sensors with their housings readily fall off the finger. It is desirable for a finger sensor to be retained on the finger with only a light pressure, while at the same time being immune to easy dislocation.

The prior art sensors with their high profile also exhibit a relatively high inertia of the housing relative to the finger. This results in a susceptibility to relative motion between the sensor and the finger as the finger is moved. This relative motion manifests itself in motion artifacts in the detected optical signals. It would be desirable for a finger sensor to be as light as possible so as to minimize relative inertial motion between the sensor and the finger.

A finger sensor meeting many of these requirements is described in U.S. patent application Ser. No. 107,085, filed Oct. 8, 1987 and entitled "PULSE OXIMETER SENSOR." The finger sensor described in this application is very light and may be applied with an adjustable pressure as determined by the tightness with which the sensor is wrapped about the finger. However, two hands are usually required to wrap the sensor about the finger and secure its Velcro TM fastening mechanism. Furthermore, the Velcro TM fastener can become soiled through repeated use. It would be desirable for a finger sensor to have a simple fastening mechanism which secures the sensor on the finger with one hand. It would further be desirable for the finger sensor to use a fastening mechanism which does not become easily soiled after repeated use.

In accordance with the principles of the present invention, a finger sensor for a pulse oximetry system is provided which comprises a soft molded shell of a polymeric material. The molded shell is sealed at its distal end and longitudinal sides, and provides a proximal opening for insertion of a finger into the pocket formed by the molded shell. Contained within the interior walls of the pocket are a photoemitter and a photodetector, which oppose each other across the interior space of the pocket. Prior to insertion of a finger, the pocket is wider than the diameter of the finger in one transverse direction, and narrower than the diameter of the finger in the other transverse direction. The insertion of the finger expands the pocket to a more rounded configuration, and the resiliency of the polymeric material retains the sensor on the finger. The finger sensor is light in weight and low in profile.

In preferred embodiments, the longitudinal sides of the sensor comprise expansive side panels which expand to accommodate the pocket to the dimensions of an inserted finger, and also resiliently retain the major walls of the pocket bearing the photoemitter and photodetector in contact with the finger. This construction enables the finger sensor of the present invention to securely accommodate fingers of a wide range of sizes. In one embodiment the expansive side panels are molded as semi-tubular regions, giving the pocket, when viewed in cross-section, the appearance of a central pocket region containing the photoemitter and photodetector and two peripherally adjoining tubular pockets. Smaller fingers will be retained by the resiliency of the polymeric central pocket with the peripheral pockets substantially closed at their interfaces with the central pocket. Larger fingers will cause the interfaces between the central and peripheral pockets to expand to accommodate the larger finger size as the interface regions conform the central pocket to the rounded shape of the finger. In a second embodiment the side panels are formed of elastomeric material which stretches when the sensor is engaged by a finger. In a third embodiment the side panels are formed of a longitudinally pleated, accordion-like material. These embodiments provide increased contact area to improve attachment, and a simplified, low-cost construction.

Figure 1:
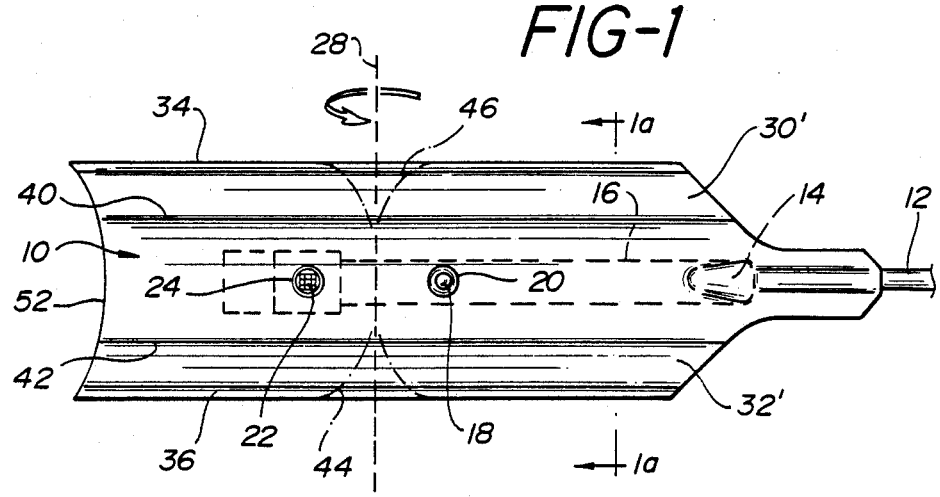
FIG. 1 illustrates a plan view of a finger sensor of the present invention prior to sealing the longitudinal sides.

Referring first to FIG. 1, a finger sensor of the present invention is shown prior to sealing the longitudinal edges 34 and 36. FIG. 1 is a plan view of the inner, finger contacting side 10 of the sensor. The sensor includes a multiwire cable 12 which is attached at a junction 14 to a flexible strip 16 of a plastic substrate on which are printed a number of metallic conductors. Alternatively, a number of discrete wires can be used in place of the flexible printed wiring strip. The flexible strip 16 is sandwiched inside the molded polymeric body of the sensor, and extends from the junction 14 to make connection to two LED's 18 and a photodetector 22. Overlying the LED's 18 and photodetector 22 in the inner surface 10 are two clear plastic windows 20 and 24 which are transmissive to light at the frequencies of the LED's 18.

The polymeric body of the sensor is molded to form several undulations across the body. Located just inside the two longitudinal edges 34 and 36 are two longitudinal concave depressions 30' and 32'. Each of these depressions forms one-half of a peripheral side panel pocket 30 and 32 when the molded body is folded and sealed. Each of the depressions 30' and 32' terminates at a smaller convex depression 40 and 42 located on each side of the central pocket wall 54 of the molded body. The end of the body remote from the cable 12 is curved as shown at 52. The body is folded in preparation for sealing at a central fold line indicated by dashed line 28. If desired, the closed end of the sensor may be gently rounded by cutting in the folded region as indicated by cutting lines 44 and 46.

Figure 1A:
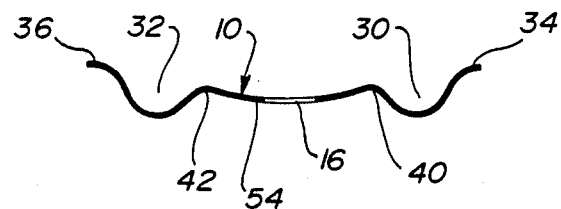
FIG. 1a illustrates the finger sensor of FIG. 1 in cross-section.

The undulations of the molded body are clearly shown in the cross-sectional view of FIG. 1a. In this view the inner surface 10 is oriented toward the bottom of the FIGURE. This cross-sectional view shows the longitudinal sealing edges 34 and 36, the peripheral side panel pocket halves 30 and 32, and the depressions 40 and 42 at the sides of the central pocket wall 54.

Figure 2:
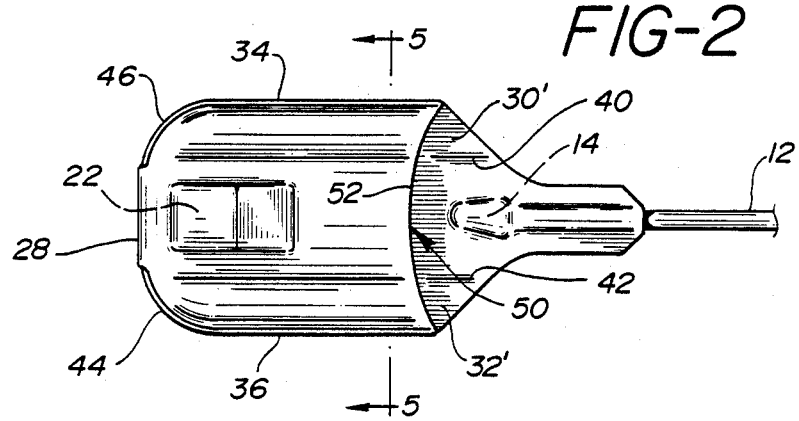
FIG. 2 is a top plan view of the finger sensor of FIG. 1 after the longitudinal sides have been sealed.

When the sensor of FIG. 1 is folded at the fold line 28 and sealed at the longitudinal edges 34 and 36, it appears as shown in FIG. 2. The longitudinal edges may be sealed by any appropriate, known technique such as by adhesives, ultrasonic or r.f. sealing, or induction sealing. The preferred technique for sealing the polymeric materials of the FIG. 2 embodiment is heat sealing. In this view the outline of the sandwiched cable 12 and junction 14 may be seen, as well as the outline of the photodetector 22. The longitudinal depressions 30' and 32' which form the peripheral side panel pockets may be seen extending into the enclosed interior 50 of the sensor. The peripheral and central pockets of the sensor terminate at the curved pocket edge 52.

Figure 3:
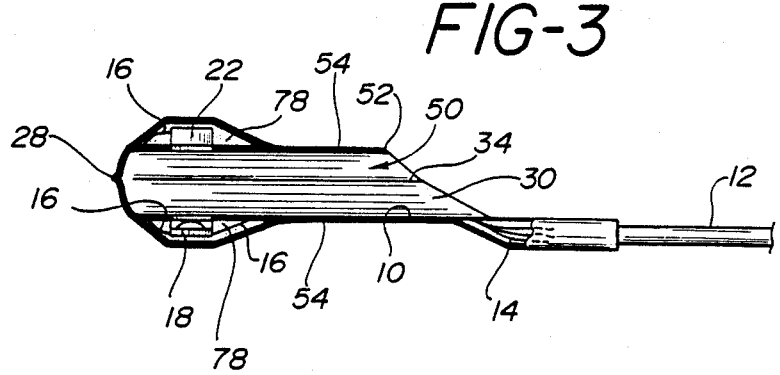
FIGS. 3 and 4 are cross-sectional views of the sensor of FIG. 2.

The completed sensor of FIG. 2 is shown in longitudinal cross-section in FIG. 3. This FIGURE shows the finger-enclosing interior 50 of the sensor formed by heat-sealing the overlapping edges 36. The LED's 18 and the photodetector 22 are seen to directly oppose each other, so that light transmitted by the LED's will be received by the photodetector after passing through a finger. The LED's and photodetector are embedded in a filler of clear silicone rubber as shown at 78. The connection of the cable wires to the flexible printed wiring is shown at the junction 14, which is also filled with silicone rubber.

Figure 4:
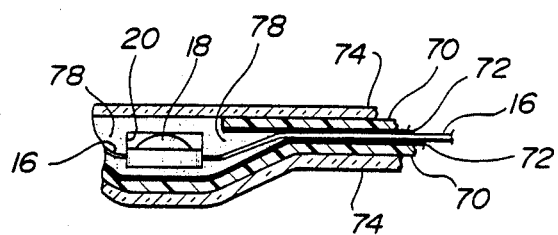

The construction of the molded polymeric body is shown in the enlarged cross-sectional view of FIG. 4, which is an enlargement of the LED region of FIG. 3. The interior of the body is formed b overlapping 0.0035 inch thick layers of opaque PVC material 72. In the preferred embodiment the PVC material is made opaque by adding aluminum powder to the PVC polymer during the extrusion process. This opaque layer 72 prevents ambient light from passing through to the interior of the sensor and degrading the reception of LED light by the photodetector. Carbon may also be used as an opacifier but is less preferred for a finger sensor because the black color may draw body heat from the finger. The aluminum powder will tend to reflect body heat back into the finger. Another technique for opacifying the layer 72 is to coat the layer with a metallic coating.

The opaque PVC layers are sandwiched between 0.010 inch thick layers of white PVC material 70. These layers provide the interior and exterior of the sensor with a characteristic white appearance. Overlying the white layers 70 are inner and outer layers of a 0.010 inch thick clear PVC material 74. These clear layers give the sensor body a shiny appearance, and function to protect labelling printed on the outside of the sensor on the white PVC layer. At the inner surface 10 of the sensor the opaque layer 72 and the white layer 70 are cut away to form the windows for the LED's and the photodetector. The clear PVC layer 74 and the clear silicone filler material 78 then will form the clear windows over the LED's and the photodetector.

As shown in FIG. 4, the LED's and the photodetector are bonded to the printed conductors on the flexible strip 16. The strip 16 is sandwiched inside the overlapping layers 72 of opaque PVC, as are the silicone rubber filler 78, the junction 14 and connecting end of the cable 12.

Figure 5:
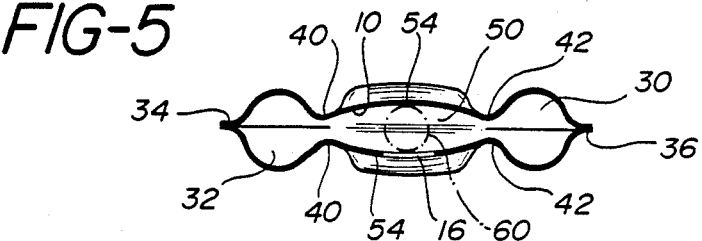
FIG. 5 is an unexpanded cross-sectional view of the sensor of FIG. 2.

The completed sensor of FIG. 2 is shown unexpanded in FIG. 5. This FIGURE shows that the interior 50 of the sensor comprises a central pocket region 54 extending from the depressions 40 on one side to depressions 42 on the other side. Located to either side of the central pocket region 54 are the peripheral side panel pockets 30 and 32. It may be seen that the unexpanded central pocket has a relatively small maximum opening dimension indicated by the broken circle 60, which in a constructed embodiment measures approximately one-quarter inch across the circle 60.

Figure 6:
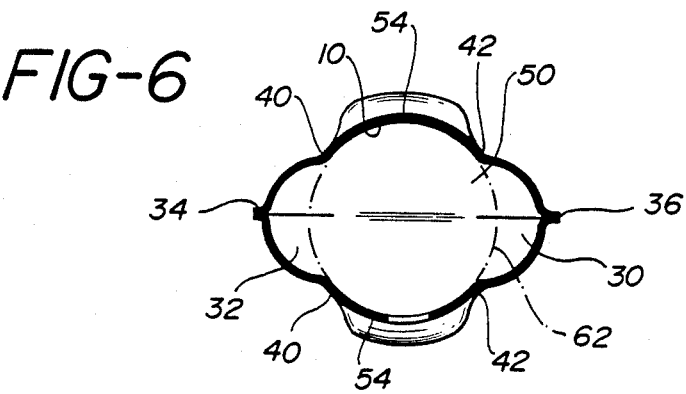
FIG. 6 is a cross-sectional view of the sensor of FIG. 2 when expanded to accommodate an adult's finger.

FIG. 6 shows the sensor when the interior 50 is engaged by a large adult finger, represented by the broken circle 62. As FIG. 6 shows, the sensor pocket enlarges due to the expansion of the peripheral pockets 30 and 32 in concert with the expansion of the central pocket region 54. The peripheral pockets expand as required to accommodate the finger, and the depressions 40 and 42 continue to define the edges of the central pocket region 54. The depressions 40 and 42 thereby engender a curvature of the central pocket walls 54, a curvature which conforms the LED's and photodetector in contact with the surface of the finger. Thus, the LED's and photodetector are securely in contact with the finger, even when the peripheral pockets 30 and 32 are not fully expanded to contact the finger. The shaded circle 62 of FIG. 6 represents the sensor of the present invention when engaged by a finger having a diameter of 0.86 inches.

In a constructed embodiment the sensor of FIG. 2 had a length of 3¼ inches and a width between the heat sealed edges 34 and 36 of 1.36 inches. The unexpanded central pocket region 54 had a width of 0.60 inches between the depressions 40 and 42. The sensor was found to securely stay on fingers of varying sizes due to the resilient "memory" of the molded polymeric material.

Figure 7:
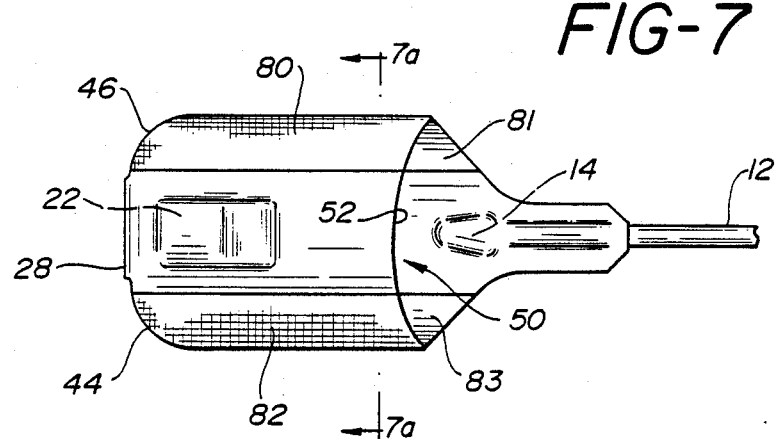
FIGS. 7 and 7a illustrate a second embodiment of the present invention in which the pocket side panels are formed of an elastomeric material.
Figure 7A:
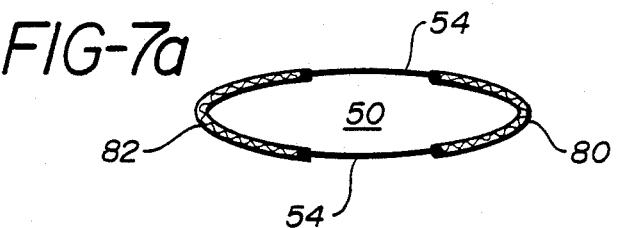

A second embodiment of the present invention is shown in the plan view of FIG. 7 and in cross-section in FIG. 7a. In this embodiment the expansive side panels of the finger sensor are formed of an opaque elastomeric material which will stretch when the sensor is engaged by a finger. The elastomeric side panels 80 and 82 may be formed of a material such as latex or elastic polyurethane. To provide the desired opacity the elastomeric material may be opacified on its inside surface by bonding to a similarly elastic opaque layer. A single layer construction as shown in FIGS. 7 and 7a may be attained by combining the opacifier such as aluminum powder in the elastomeric material during the extrusion process.

In the embodiment of FIG. 7, like reference numerals are used to refer to the same structures shown in FIG. 2. The elastomeric side panels 80 and 82 are bonded at their longitudinal junctures with the central pocket region 54 by overlapping and embedding the edges of the central pocket material in the elastomeric material, as shown in FIG. 7a. In FIG. 7a the overlapping regions are exaggerated in thickness to more clearly illustrate the sandwiched construction; in an actual constructed embodiment the junctures would result in a smoothly continuous bond. The central pocket region between the side panels is formed of the same layered materials shown in FIG. 4. In the cross-sectional view of FIG. 7a it may be seen that this embodiment is formed as a smoothly continuous eliptically-shaped pocket 50.

Figure 8:
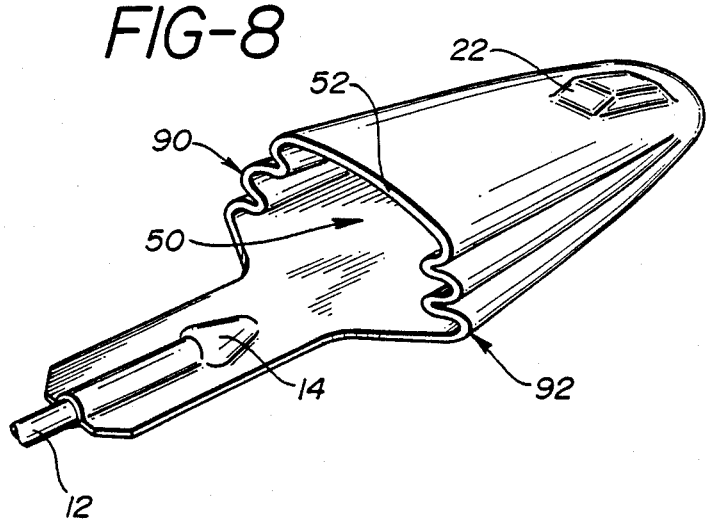
FIG. 8 illustrates a third embodiment of the present invention in which the Pocket side panels are formed as longitudinal pleats.

A third embodiment of a finger sensor of the present invention is shown in FIG. 8. In this embodiment the expansive side panels are formed as longitudinal pleats molded in the polymeric material as shown at 90 and 92. In the view of FIG. 8 the pleated sides are shown partially opened as they would be when the sensor is engaged by a finger. Prior to insertion the accordion-like pleats would be virtually completely collapsed by the resilience of the pleated material.

Like the previous embodiment the pleated side panels are opacified by a bonded opaque layer or by the inclusion of an opacifying material in the polymer itself. In FIG. 8 the pleated side panels 90 and 92 are formed of the same molded opaque, white, and clear PVC layers as shown in the sandwiched construction of FIG. 4. In a folded and sealed embodiment the sealing seam would run longitudinally along the pleats on the opposing sides of the pocket.

What is claimed is:

1. In apparatus for sensing light absorption through transillumination of blood perfused flesh by a light source and reception of light by an optical detector; a finger sensor comprising a sheet of flexible polymeric material which is overlapped and sealed about its periphery to form a pocket having a longitudinal length and an opening at one end of said length having a smaller width and a greater width, said pocket enclosing and retaining a light source and an optical detector which oppose each other from interior walls of said pocket, and a cable connected to said light source and said optical detector, said pocket having a resiliency such that, when a finger is inserted into said pocket to a position between said light source and said optical detector so as to expand said smaller width and decrease said greater width, said pocket has a tendency to oppose said expansion and said decrease.

2. The apparatus of claim 1, wherein said interior walls of said pocket are formed in a generally convex shape to conform to the shape of a finger.

3. The apparatus of claim 1, further comprising a pair of expansive longitudinally extending side panels located at opposite ends of said greater width dimension of said pocket.

4. The apparatus of claim 3, wherein said pocket comprises a relatively large central longitudinally extending pocket region adjoined on either side by relatively smaller peripheral longitudinally extending side panel pocket regions,
wherein said greater width dimension intersects said central pocket region and said peripheral side panel pocket regions.

5. The apparatus of claim 4, wherein said smaller width dimension is relatively smaller at each jointure of a peripheral pocket region with the central pocket region, and is relatively larger in the center of each of said pocket regions.

6. The apparatus of claim 5, wherein said pocket expands when engaging a finger by the expansion of said peripheral pocket regions in concert with relatively greater expansion of said central pocket region.

7. The apparatus of claim 5, wherein, when said pocket is expanded to less than its fullest capacity, the walls of said central pocket region are in contact with said finger and the walls of said peripheral pocket regions are not in contact with said finger.

8. The apparatus of claim 3, wherein said side panels are formed of an elastomeric material.

9. The apparatus of claim 17, wherein said elastomeric material is opacified by the inclusion of an opacifier in said elastomeric material.

10. The apparatus of claim 8, wherein said elastomeric material is bonded to a similarly elastic opaque layer.

11. The apparatus of claim 8, wherein said light source and said optical detector are retained by major walls of said pocket at opposite ends of said smaller width dimension, and said elastomeric side panels longitudinally connect said major walls at opposite ends of said greater width dimension,
wherein said major walls are relatively inelastic as compared with said elastomeric material.

12. The apparatus of claim 3, wherein said side panels are formed of a pleated material;
wherein the folds of said pleats extend longitudinally.

13. The apparatus of claim 12, wherein said pleated material is opacified by the inclusion of an opacifier in said pleated material.

14. The apparatus of claim 12, wherein said pleated material is bonded to an opaque layer.

15. The apparatus of claim 12, wherein said light source and said optical detector are retained by major walls of said pocket at opposite ends of said smaller width dimension, and said pleated side panels longitudinally connect said major walls at opposite ends of said greater width dimension,
wherein said longitudinal pleats unfold to allow expansion of said pocket when engaged by a finger.

16. The apparatus of claim 1, wherein said sheet of polymeric material is opaque.

17. The apparatus of claim 16, wherein said sheet of polymeric material is made opaque by a metallic compound included in said polymeric material.

18. The apparatus of claim 17, wherein said sheet of polymeric material further includes an outer layer of a colored polymeric material.

19. The apparatus of claim 18, wherein said sheet of polymeric material further includes an inner layer of clear polymeric material.

20. The apparatus of claim 18, wherein the color of said colored polymeric material is white.

21. The apparatus of claim 1, further comprising means for electrically connecting said cable with said light source and said optical detector,
   wherein said connecting means is enclosed within said sheet of polymeric material.

22. The apparatus of claim 1, wherein said pocket is formed by a single sheet of polymeric material which is folded between said light source and said optical detector with the fold forming the nd of said pocket opposite said opening, the opposing longitudinal edges of said folded sheet being sealed to form said pocket.

23. The apparatus of claim 22, wherein said opposing longitudinal edges of said folded sheet are sealed by heat sealing.

24. The apparatus of claim 22, wherein said sheet is trimmed on either side of said fold so as to form a generally rounded shape at the fold end of said pocket.

* * * * *